(12) United States Patent
Kratz

(10) Patent No.: US 7,387,771 B1
(45) Date of Patent: Jun. 17, 2008

(54) METHOD FOR PRODUCING AN INJECTABLE MEDICAMENT PREPARATION

(75) Inventor: Felix Kratz, Freiburg (DE)

(73) Assignee: KTB Tumorforschungs GmbH, Freiburg (DE)

( * ) Notice: Subject to any disclaimer, the term of this patent is extended or adjusted under 35 U.S.C. 154(b) by 128 days.

(21) Appl. No.: 09/980,266

(22) PCT Filed: Jun. 7, 2000

(86) PCT No.: PCT/EP00/05272

§ 371 (c)(1),
(2), (4) Date: Nov. 30, 2001

(87) PCT Pub. No.: WO00/76551

PCT Pub. Date: Dec. 21, 2000

(30) Foreign Application Priority Data

Jun. 9, 1999 (DE) ................................. 199 26 154

(51) Int. Cl.
*A61K 51/00* (2006.01)
(52) U.S. Cl. ........................... 424/1.11; 530/350; 514/2
(58) Field of Classification Search ........................ None
See application file for complete search history.

(56) References Cited

U.S. PATENT DOCUMENTS

| 5,606,017 | A | 2/1997 | Willner et al. |
| 5,622,929 | A | 4/1997 | Willner et al. |
| 5,708,146 | A | 1/1998 | Willner |

FOREIGN PATENT DOCUMENTS

| DE | 196 36 889 | 3/1998 |
| DE | 199 23 168 A1 | 11/2000 |
| EP | 0 554 708 B1 | 5/2005 |
| WO | 00 76550 | 12/2000 |

OTHER PUBLICATIONS

Kratz., et al "Preparation, Characterization and In Vitro . . . Doxorubicin", Biological & Pharm. Bulletin, Pharm. Soc. of Japan, vol. 21, No. 1 , 1998, pp. 56-61.
A. Trouet, et al. "A covalent linkage between daunorubicin and proteins that is . . . in vivo studies", Proceedings of the National Academy of Sciences of USA, vol. 79, 1 82 (pp. 626-629.
S. Netzel-Arnett, "Comparative Sequence . . . (Matrilysin", Biochemistry, vol. 32, No. 25, 1993, pp. 6427-6432.
M. Nichifor et al: "Macromolecular prodrugs of 5-fluoroouracil . . . degradation", Journal of Controlled release, vol. 39, 1996, pp. 79-92.
G. M. Dubowchik et al: "Cathepsin B-sensitive dipeptide prodrugs. 1. A model study . . . doxorubicin", Biorg. Med. Chem. Lett. vol. 8. No. 23, pp. 3341-3346.
M. Kruger, et al: "synthesis and stability of four maleimide . . . chemoimmunoanjugates", Biological & Pharm. Bull. of Japan, vol. 45, No. 2, 1997, pp. 399-401.
Beyer, et al., "Synthesis of New Bifunctional Maleimide Compounds for the Preparation of Chemoimmunoconjugates", *Monatshefte für Chemie* 128, pp. 91-102 (1997), Austria.
Kruüger, et al., "Synthesis and Stability of Four Maleimide Derivatives of the Anticancer Drug Doxorubicin for the Preparation of Chemoimmunoconjugates", *Chem. Pharm. Bull*45(2) pp. 399-401 (1997).
Wilner, et al., "(6-Maleimidocaproyl)hydrazone of Doxorubicin-a New Derivative for the Preparation of Immunoconjugates of Doxorubicin", *Bioconjugate Chem*. 1992, 4, pp. 521-527.

*Primary Examiner*—Christopher Tate
*Assistant Examiner*—Roy Teller
(74) *Attorney, Agent, or Firm*—Fulbright & Jaworski L.L.P.

(57) ABSTRACT

The invention relates to a method for producing injectable medicament preparations containing a therapeutically and/or diagnostically effective substance which is comprised of an active agent, of a spacer molecule and of at least one protein-binding molecule. After being brought into contact with the body, said therapeutically and/or diagnostically effective substance covalently bonds to the body fluid constituents or tissue constituents via the protein-binding molecules, thus providing a form of transport of the active agent that can be hydrolytically or enzymatically cleaved, according to pH, in the body while releasing the active agent.

10 Claims, 7 Drawing Sheets

METHOD FOR PRODUCING AN INJECTABLE MEDICAMENT PREPARATION

BACKGROUND AND SUMMARY OF THE INVENTION

The invention relates to a process for producing injectable medicament preparations which comprise a therapeutically and/or diagnostically effective substance which consists of an active compound, a spacer molecule and at least one protein-binding molecule and, after having been brought into contact with the body, binds covalently, by way of the protein-binding molecule, to body fluid constituents or tissue constituents, thereby creating a transport form of the active compound which can be hydrolytically or enzymically cleaved, in a pH-dependent manner, in the body with the active compound being released.

Most of the drugs which are used at present are low molecular weight compounds and, after having been administered systemically, exhibit high plasma and total clearances. Furthermore, as a result of diffusion processes, they penetrate into the tissue structures of the body and as a rule have a uniform biodistribution. These two properties lead to only small quantities of the drug reaching the site of action and, because of its distribution over the healthy tissue of the body, the drug gives rise to side-effects. These disadvantages are particularly pronounced in the case of those drugs which possess a high cytotoxic potential, such as cytostatic agents, immunosuppressive agents or virostatic agents.

Several strategies are pursued for improving the selectively of low molecular weight drugs, for example the chemical derivatization of basic structures, formulation as prodrugs, or the coupling of the drugs to carrier molecules. The present invention takes as its starting point those concepts in which drugs have been chemically bonded to endogenous macromolecules. Conjugates are known in which what are in general cytostatic agents are bound to serum proteins, predominantly to particular carrier molecules such as human serum albumin and human serum transferin, and then administered. These known protein conjugates are prepared either by coupling the cytostatic agent to the serum protein ex vivo in a "one pot method" (DE 41 22 210 A1), and isolating the resulting albumin-cytostatic agent conjugate, or by firstly derivatizing the cytostatic agent with a suitable spacer molecule, isolating the resulting product and, in a second step, coupling the cytostatic agent which has been derivatized in this way to the protein by way of a maleimide group (DE 196 36 889 A1 and PCT/DE97/02000) and then isolating the resulting albumin-cytostatic agent conjugate. Both methods suffer from the disadvantage that they use plasma proteins, which may contain pathogens. Other disadvantages of the above-described protein-active compound conjugates are their unsatisfactory stability and shelf-life and the technical input required for preparing them.

The invention is based on the object of overcoming these disadvantages. This object is achieved by means of a process for producing an injectable medicament preparation, comprising a therapeutically and/or diagnostically effective substance which is dissolved in an injectable carrier liquid, which process is characterized in that use is made, as the therapeutically and/or diagnostically effective substance, of a compound which consists of an active compound and at least one protein-binding molecular residue which are linked by way of a spacer, in which the spacer, or the bond between the active compound and the spacer, can be cleaved hydrolytically or enzymatically in the body in a pH-dependent manner. The active compound, or a derivative of the active compound, is released during the cleavage. An active compound derivative is understood as meaning substances which include the active compound but which may additionally contain parts of the spacer or of the groups by which the active compound was bonded to the protein-binding molecule. The activity of the active compound should not be impaired as a result of being released as a derivative. The active compound, or its derivative, preferably only displays its activity after having been released.

The invention is based on the surprising observation that it is not necessary, as had previously been assumed, to link an active compound to a particular carrier under defined conditions and then to administer the product but that, on the contrary, it is possible to employ therapeutically and/or diagnostically effective substances, which consist of a pharmacological active compound and at least one protein-binding molecular moiety, which are linked to each other by way of a spacer, directly as injectable medicaments since these medicaments, after having been brought into contact with the body, bind covalently, by way of the protein-binding molecule, to body fluid or tissue constituents, predominantly to serum proteins, such that a transport form of the active compound is created in vivo, which transport form reaches the cells or the tissue which is/are the target of the active compound. Since, in the case of the substance which is therapeutically and/or diagnostically effective, the bond in the spacer molecule, or between the active compound and the spacer molecule, can be cleaved, according to the invention, hydrolytically or enzymatically in the body in a pH-dependent manner, the active compound is nevertheless released, in a selective manner, at the desired target site.

Because of their protein-binding properties, injectable medicament preparations, which are obtained in accordance with the invention, of therapeutically and/or diagnostically effective substances decisively alter and improve the pharmacokinetic profile of the active compounds. When these therapeutically and/or diagnostically effective substances arrive in body fluids, they bind covalently to body fluid or tissue constituents, preferably to serum proteins, more preferably to serum albumin, in order, in this way, to be present as macromolecular prodrugs which transport the active compound to the target site and/or release it in a metered form.

The therapeutically and/or diagnostically effective substance which is obtained in accordance with the invention consists of an active compound A, a spacer molecule SM and at least one protein-binding molecule PM, having the following general structure:

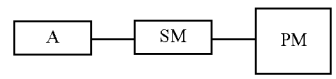

In addition, the substance which is obtained in accordance with the invention can possess labelling groups or labelled elements or molecules, with the substance then being particularly suitable for diagnostic purposes. Preferred labels are one or more radionuclides, one or more ligands comprising radionuclides, one or more positron emitters, one or more NMR contrast agents, one or more fluorescent compound(s) and/or one or more contrast agents in the near IR range.

DETAILED DESCRIPTION

Figure 1:
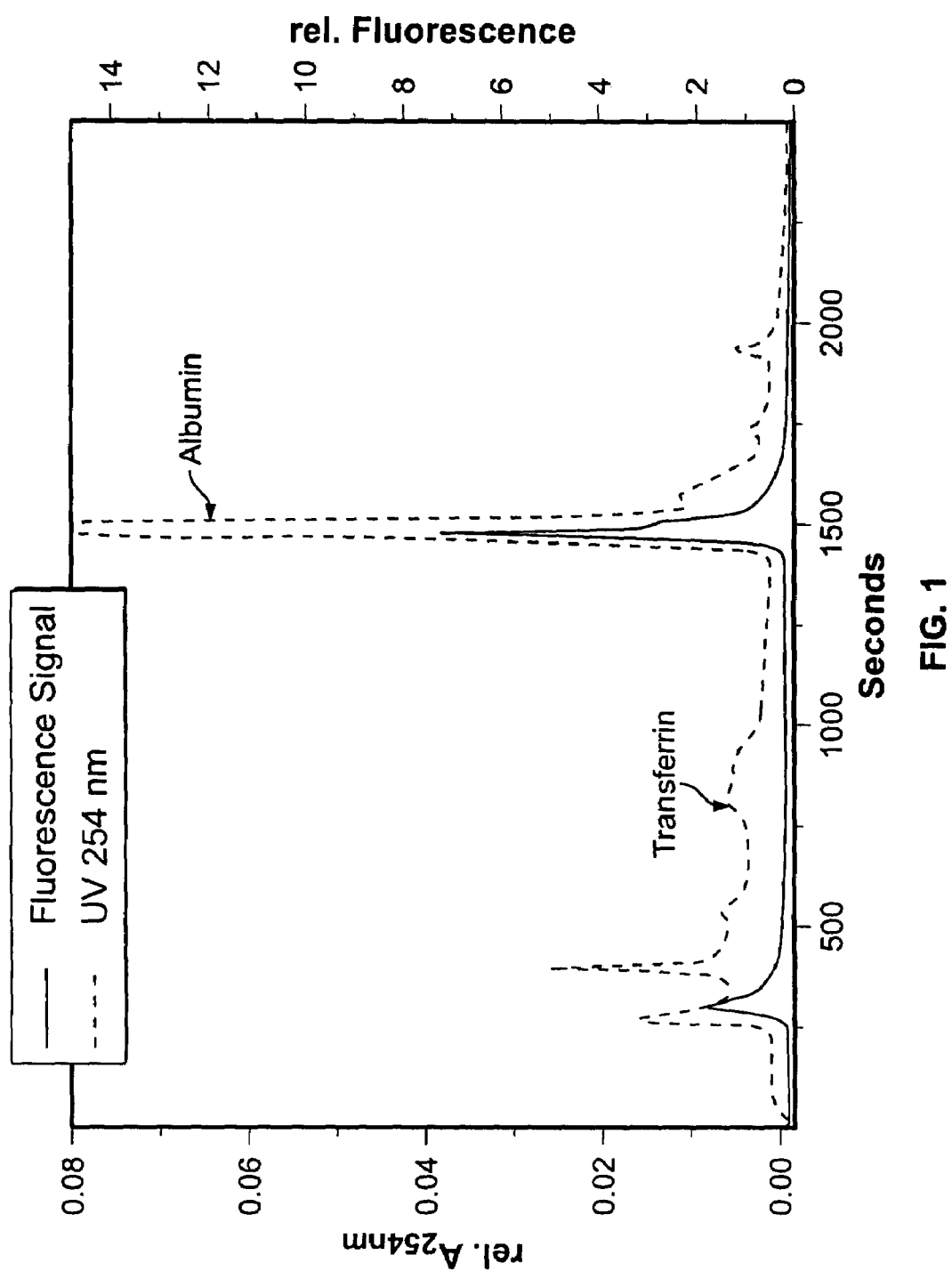
FIGS. 1 and 1a are chromatograms showing the results of Example 2.

Within the meaning of this invention, a diagnostic agent is, for example, a labelled active compound as described above or one or more fluorescent compound(s) and/or one or more contrast agents in the near IR range.

The active compound is a cytostatic agent, a cytokine, an immunosuppressive agent, a virostatic agent, an antirheumatic agent, an analgesic, an antiinflammatory agent, an antibiotic, an antimycotic agent, a signal transduction inhibitor, an angiogenesis inhibitor or a protease inhibitor.

Cytostatic agents which are preferred for preparing injectable, therapeutically and/or diagnostically effective substances according to the present invention are the anthracyclines doxorubicin, daunorubicin, epirubicin, idarubicin, mitoxantrone and ametantrone, and also related derivatives, the alkylating agents chlorambucil, bendamustin, melphalan and oxazaphoshorins and also related derivatives, the antimetabolites methotrexate, 5-fluorouracil, 5'-deoxy-5-fluorouridine and thioguanine, and also related derivatives, the taxanes paclitaxel and docetaxel, and also related derivatives, the camptothecins topotecan, irinotecan, 9-aminocamptothecin and camptothecin, and also related derivatives, the podophyllotoxin derivatives etoposide, teniposide and mitopodozide, and also related derivatives, the vinca alkaloids vinblastine, vincristine, vindesine and vinorelbine, and also relative derivatives, the calicheamicins, the maytansinoids and a compound of the general formula I to XII:

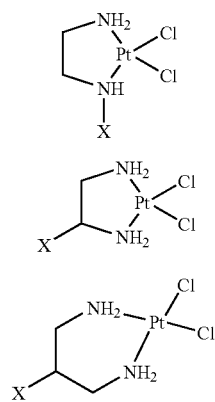

formula I formula II formula III where X denotes the spacer molecule SM or the protein-binding molecule PM.

Cytokines which are preferred for preparing therapeutically and/or diagnostically effective substances of the present invention are interleukin 2, interferon β-2a, interferon α-2b, interferon β-1a,

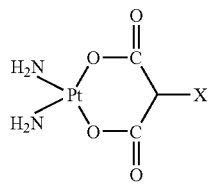 formula IV

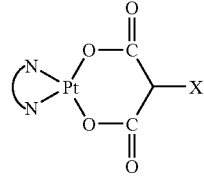 formula V

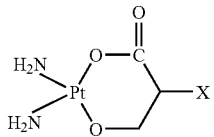 formula VI

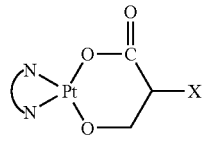 formula VII

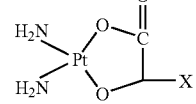 formula IX

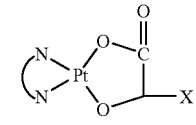 formula X

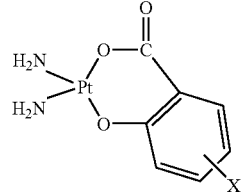 formula XI formula XII

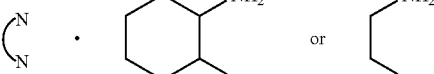

Interferon β-1b, interferon γ-1b, and related derivatives. The cytokines employed are as a rule recombinantly produced medicaments.

Immunosuppressive agents which are preferred for the process of the present invention are cyclosporin A and related derivatives, and also tacrolimus (FK 506) and related derivatives.

Antirheumatic agents which are particularly suitable for the process of the present invention are methotrexate and related derivatives.

Analgesic agents which are preferred for the process of the present invention are salicylic acid derivatives, such as acetylsalicylic acid and related derivatives, drug derivatives which possess an acetic acid or propionic acid group, such as diclofenac or indomethacin or ibuprofen or naproxen, and aminophenol derivatives, such as paracetamol.

Antimycotic agents which are preferred for the process of the present invention are amphotericin B and related derivatives.

Virostatic agents which are preferred for the process of the present invention are nucleoside analogues, such as aciclovir, ganciclovir, idoxuridine, ribavirin, vidaribine, zidovudine, didanosine and 2',3'-dideoxycytidine (ddC), and related derivatives, and amantadine.

Antibiotics which are preferred for the process of the present invention are sulphonamides, such as sulanilamide, sulphacarbamide and sulphamethoxydiazine and related derivatives, penicillins, such as 6-aminopenicillanic acid, penicillin G and penicillin V, and related derivatives, isoxazoylpenicillins (e.g. oxacillin, cloxacillin, flucloxacillin), and related derivatives, -substituted benzylpenicillins (e.g. ampicillin, carbenicillin, pivampicillin and amoxicillin), and related derivatives, acylaminopenicillins (e.g. mezlocillin, azlocillin, piperacillin and apalicillin), and related derivatives, amidinopenicillins, such as mecillinam, atypical β-lactams, such as imipenam and aztreonam, cephalosporins, such as cefalexin, cefradine, cefaclor, cefadroxil, cefixime, defpodoxime, cefazolin, cefazedone, cefuroxime, cefamandole, cefotiam, cefoxitin, cefotetan, cefinetazole, latamoxef, cefotaxime, ceftriaxone, ceftizoxime, cefmonoxime, ceftazidime, cefsulodin and cefoperazone, and related derivatives, tetracyclines, such as tetracycline, chlortetracycline, oxytetracycline, demeclocycline, rolitetracycline, doxycycline and minocycline, and related derivatives, chloramphenicols, such as chloramphenicol and thiamphenicol, and related derivatives, gyrase inhibitors, such as nalixidic acid, pipemidic acid, norfloxacin, ofloxacin, ciprofloxacin and enoxacin, and related derivatives, and tuberculosis agents, such as isoniazid and related derivatives.

The spacer molecule SM is an organic molecule which consists of an aliphatic carbon chain and/or an aliphatic carbon ring and/or at least one aromatic compound. The carbon chain/ring preferably consists of 1-12 carbon atoms, some of which may be replaced by oxygen atoms, and can, where appropriate, be substituted, particularly by one or more water-soluble groups, such as sulphonic acid, aminoalkyl or hydroxyl groups. The aromatic compound is preferably a benzene ring which can, where appropriate, be substituted, for example by the abovementioned water-soluble group. To improve its water solubility, the aliphatic carbon chain can contain oxygen atoms and be expediently derived, for this purpose, from an oligoethylene oxide or oligopropylene oxide chain, for example a diethylene glycol, triethylene glycol or dipropylene glycol chain.

The protein-binding molecule PM is preferably a maleimide group, a haloacetamide group, a haloacetate group, a pyridyldithio group, an N-hydroxysuccinimide ester group or an isothiocyanate group. It can also be a disulphide group, a vinylcarbonyl group, an aziridine group or an acetylene group. The disulphide group is preferably activated, as a rule by a thionitrobenzoic acid (e.g. 5'-thio-2-nitrobenzoic acid) being the exchangeable group. The groups may be substituted, where appropriate. The maleimide, pyridyldithio or N-hydroxysuccinimide ester group can, where appropriate, be substituted by alkyl or by the abovementioned water-soluble groups. The PM possesses protein-binding properties, i.e., it binds covalently, in a physiological environment, to particular amino acids on the surface of the protein. In this connection, the maleimide group, the haloacetamide group, the haloacetate group, the pyridyldithio group, the disulphide group, the vinylcarbonyl group, the aziridine group and/or the acetylene group preferably reacts with HS groups of cysteines, while the N-hydroxysuccinimide ester group and the isothiocyanate group preferably react with the amino group of lysines, on the surface of the protein.

Following parenteral administration, the therapeutically and/or diagnostically effective substance, which is prepared, as an injectable medicament preparation, by the process of the present invention, arrives in the blood stream and can bind to proteins by way of the PM. The binding preferably takes place to serum proteins, in particular serum albumin. It has been found that, in a physiological environment, the therapeutically and/or diagnostically effective substance reacts, by way of the maleimide group, the haloacetamide group, the haloacetate group, the pyridyldithio group, the disulphide group, the vinylcarbonyl group, the aziridine group or the acetylene group, with the free cysteine-34 of the albumin, in particular, and is in this way bound covalently. Pharmacologically active substances having an N-hydroxysuccinimide ester group or isothiocyanate group preferentially bind to the ε-amino group lf lysines on the protein surface of albumin or other serum proteins. Serum proteins, such as albumin or transferin, have a markedly long half-life in the systemic circulation (up to 19 days—Peters, T. Jr. (1985): Serum albumin. Adv. Protein. Chem. 37, 161-245). Because the permeability to macromolecules of the walls of the vessels in the malignant, infected or inflamed tissue is increased, the serum albumin preferentially makes its way into this target tissue (Maeda, H.; Matsumura, Y. Crit. Rev. Ther. Drug Carrier Sys. (1989), 6, 193-210). As a result, an active compound which is coupled to albumin is able to reach the site of action in a more targeted manner. Furthermore, the covalent coupling of the active compound to serum proteins in the blood stream prevents the active compound from diffusing into healthy tissue structures in the body or being eliminated by way of the kidneys, or damaging these tissues to the same extent as would the unbound active compound. As a result, the pharmacokinetic profile of the active compound is altered and improved since its effect is increased as a result of it being enriched at the site of action and, at the same time, the toxic effects on healthy systems in the body are diminished.

The therapeutically and/or diagnostically effective substances which are used in accordance with the present invention contain a defined chemical bond in the spacer molecule or between the SM and the A. This bond can be cleaved or hydrolytically cleaved in a pH-dependent manner, preferably in an acid-labile manner, or else it contains a bond which can be cleaved enzymatically in the body, preferably a peptide bond.

Examples of bonds which are cleaved by hydrolysis, with the active compound being released, are ester bonds or metal complex bonds, as are present in platinum-dicarboxylate complexes, with a diamminediaquo-platinum(II) complex being released. The acid-labile cleavable bonds are acetal, ketal, imine, hydrazone, carboxylhydrazone or sulphonylhydrazone bonds, or cis-aconityl bonds or bonds containing a trityl group, with it being possible for the trityl group to be substituted or unsubstituted. Preferred therapeutically/diagnostically relevant acid-labile bonds are described, for example, in Kratz et al. (1990) Crit. Rev. Ther. Drug. Car. Sys. 16 (3), 245-288. The peptide sequence in the peptide bonds which are formed consists as a rule of about 2-30 amino acids. In this connection, the peptide sequence is preferably tailor-made for the substrate specificity of particular enzymes, which are designated target enzymes in that which follows, such that the peptide sequence, or a part of this sequence, is recognized by an enzyme in the body and the peptide is cleaved. According to another embodiment of the present invention, the enzymically cleavable bond consists of a bond which is not a peptide bond. Examples are carbamate bonds, which, by the mediation of disease-specific enzymes, e.g. glutathione-S-transferases, glucuronidases and galactosidases, release the active compound or an active compound derivative. It is also readily possible for an enzymatically H and L, which have been identified as key enzymes in inflammatory and malignant diseases.

The abovementioned bond types ensure that the active compound, or a correspondingly active derivative, is released, extracellularly and/or intracellularly, following uptake of the conjugate by the cell, and can express its therapeutic and/or diagnostic effect, at the active site.

The cleavage can also take place in such a way that it is not the active compound as such which is cleaved off, but, instead, a derivative of the active compound. Such a derivative constantly contains the active compound and groups which are bonded to it and which are derived from the spacer molecule, depending on the site at which the desired cleavage has taken place.

The therapeutically and/or diagnostically effective substance which is used in the process of the present invention can be prepared in accordance with one of the general descriptions given below:

Active compounds which possess a COOH group are derivatized in the following manner:

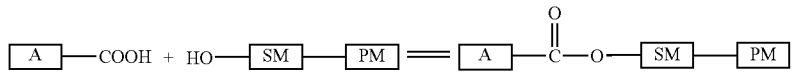

cleavable bond to be composed of a peptide sequence and one of the abovementioned bonds which is not a peptide bond. The target enzymes can be either endogenous enzymes or enzymes which occur in microorganisms or are formed by microorganisms.

The target enzymes are as a rule proteases, serine proteases, plasminogen activators and peptidases, for example matrix metalloproteases (MMP) or cysteine proteases, which are formed to an increased extent, or are activated, in association with diseases such as rheumatoid arthritis or cancer, thereby leading to excessive tissue breakdown, to inflammations and to metastases. Target enzymes are, in particular, MMP 2, MMP3 and MMP 9, which are involved, as proteases, in the abovementioned pathological processes (Vassalli, J., Pepper, M. S. (1994), Nature 370, 14-15, Brown, P. D. (1995), *Advan Enzyme Regul.* 35, 291-301).

Further proteases which constitute target enzymes for therapeutically and/or diagnostically effective substances of the present invention are cathepsins, in particular cathepsin B, In this connection, the esterification is effected using customary methods with which the skilled person is familiar.

It is furthermore possible to convert the COOH group into a hydrazide group, for example by reacting with tert-alkyl carbazates and subsequently cleaving with acids (described in DE 196 36 889), and to react the drug possessing a hydrazide group with a spacer which consists of PM and SM and which contains a carbonyl component, as described, inter alia, in DE 196 36 889 A1 and also PCT/DE 97/02000;

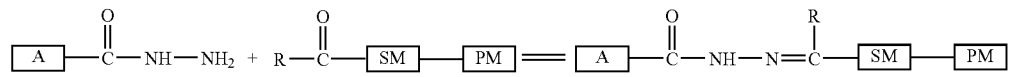

R=H, alkyl, phenyl or substituted phenyl

Active compounds of the present invention which possess an NH$_2$ group are derivatized in the following manner:

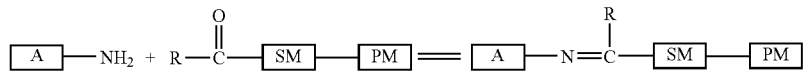

R=H, alkyl, phenyl or substituted phenyl

In this connection, the reaction to give the imine derivatives is effected using customary methods with which the skilled person is familiar.

Active compounds of the present invention which possess an OH group are derivatized in the following manner:

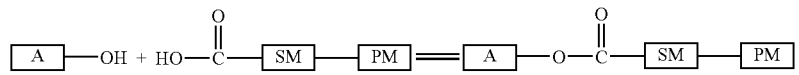

In this connection, the esterification is effected using customary methods with which the skilled person is familiar.

Active compounds of the present invention which possess a carbonyl component are derivatized in the following manner:

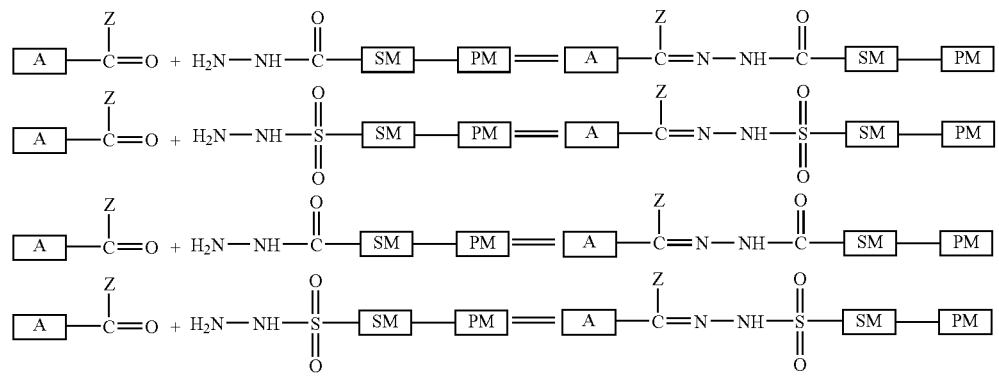

Z=chemical group belonging to the active compound

In this connection, the reaction to give the carboxyhydrazone, sulphonylhydrazone, hydrazone and/or imine derivatives takes place in accordance with methods which are described, inter alia, in DE 196 36 889 A1 and/or PCT/DE 97/02000, or using customary methods with which the skilled person is familiar.

It is furthermore possible to convert an OH group or an $NH_2$ group on an active compound into a carbonyl component, for example by means of esterification or amide formation using a carboxylic acid-carrying carbonyl component in accordance with the following general formula:

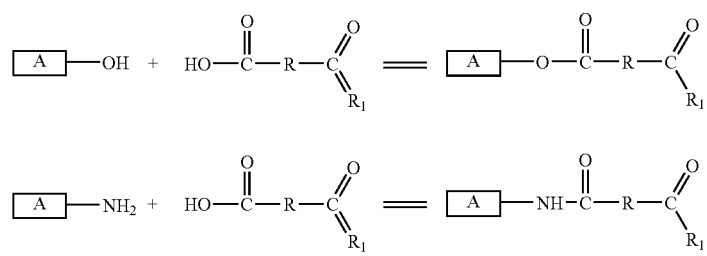

where R is an aliphatic carbon chain and/or an aliphatic carbon ring and/or an aromatic moiety and $R_1$=H, or an alkyl, phenyl or substituted phenyl group. As a rule, R consists of from 1 to 12 carbon atoms which may, where appropriate, be substituted, e.g. by water-soluble groups such as sulphonic acid, aminoalkyl or hydroxyl groups. The aromatic moiety is as a rule a benzene ring which can, where appropriate, be substituted, for example by the abovementioned water-soluble groups.

The carbonyl component can furthermore be introduced using other chemical reactions, for example by means of an electrophilic substitution at the HO or $NH_2$ group in the active compound using a suitable carbonyl component.

The active compounds which have been derivatized in this way, and which now possess a carbonyl component, are reacted, in analogy with the above-described methods, with the protein-binding binding spacer molecules, which possess an amino, hydrazide or hydrazine group, to give the corresponding carboxylhydrazone, sulphonylhydrazone, hydrazone or imine derivatives. The acid-labile cleavage of these bonds consequently leads to a release of the derivatized active compound which possesses a carbonyl component.

The spacers, which consist of the protein-binding molecule PM and the spacer molecule SM, can be prepared, for example, in accordance with methods which are described, inter alia, in DE 196 36 889 A1, U. Beyer et al. Chemical Monthly, 128, 91, 1997, R. S. Greenfield et al., *Cancer Res.*, 50, 6600, 1990, T. Kaneko et al., *Bioconjugate Chem.*, 2, 133, 1991, Bioconjugate Techniques, G. T. Hermanson, Academic Press, 1996 or in U.S. Pat. No. 4,251,445.

Therapeutically and/or diagnostically effective substances for the present invention which contain a peptide bond can be prepared by reacting a peptide, which consists of from 2 to about 30 amino acids, with a protein-binding compound such that a protein-binding molecule is introduced directly, or by way of a spacer molecule SM, at the N-terminal end of the peptide. Such protein-binding peptide derivatives are preferably synthesized using a solid phase synthesis with which the skilled person is familiar, with a carboxylic acid-carrying, protein-binding spacer molecule, for example a maleimidocarboxylic acid, being bonded, by means of peptide coupling, to the N-terminal end of the peptide in the last step of the peptide synthesis and the protein-binding peptide then being eliminated from the solid phase. The peptide derivatives which are obtained in this way can be reacted with an active compound, which possesses an NH$_2$ or OH group, in the presence of a condensing agent, such as N,N'-dicyclohexyl-carbodiimide (DCC) or N-cyclohexyl-N'-(2-morpholinoethyl)carbodiimide metho-p-toluenesulphonate (CMC), (benzotriazol-1-yloxy)trispyrrolidinophosphonium hexafluorophosphate (pyBOP) or O-benzotriazole-N,N,N',N'-tetramethyluronium hexafluorophosphate, and, where appropriate, with the addition of N-hydroxy-succinimide or of a water-soluble N-hydroxysuccinimide, such as N-hydroxysuccinimide-3-sulphonic acid sodium salt or 1-hydroxybenzotriazole and/or in the presence of a base, such as N-methylmorpholine or triethylamine, to give the corresponding protein-binding active compound-peptide derivatives:

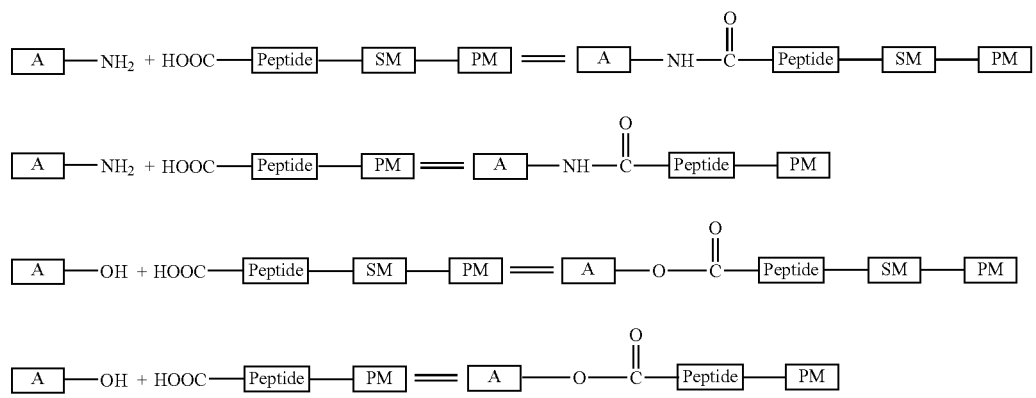

It is furthermore possible to introduce an NH$_2$ or OH group by way of the COOH group which is present on the active compounds, for example by means of derivatizing with the amino acids (AA) lysine, serine or threonine by way of their -amino group or by way of the α-amino group using a diamino compound of the general formula H$_2$N—(CH$_2$)$_n$—NH$_2$ or using an alcoholamine of the general formula H$_2$N—(CH$_2$)n—OH, where n=1-12, and subsequently reacting these derivatives with the abovementioned peptide derivatives to give the corresponding protein-binding active compound-peptide derivatives:

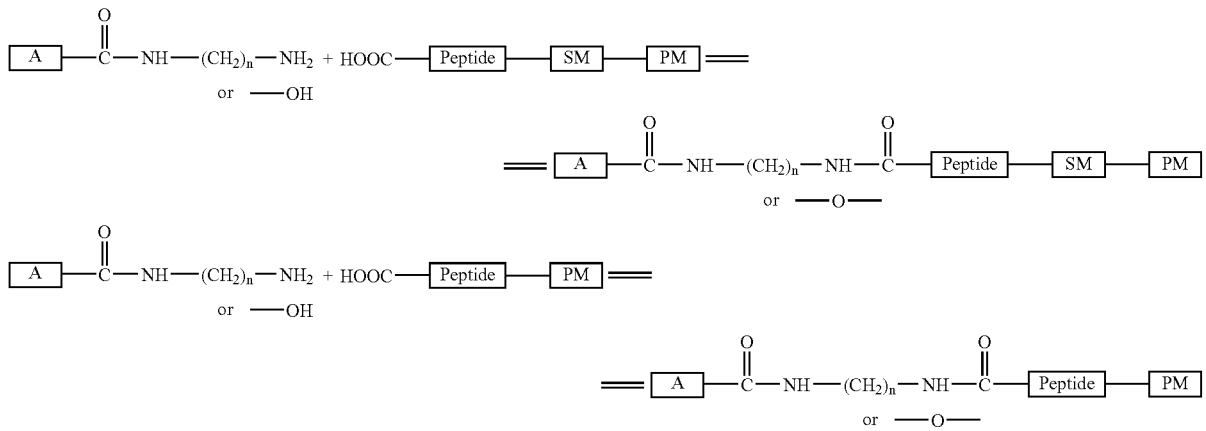

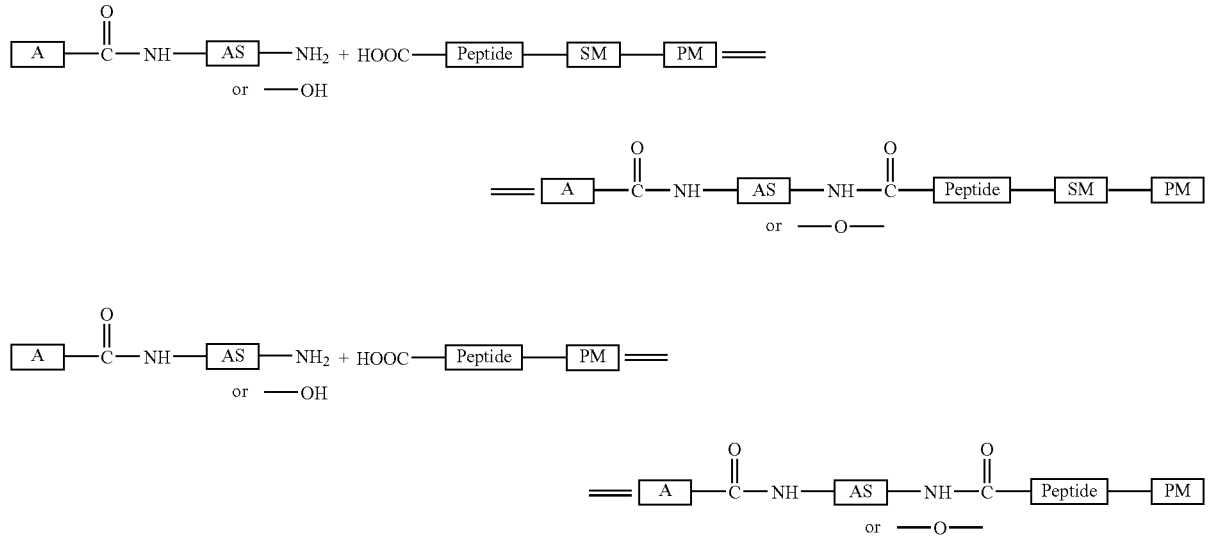

AA=lysine, serine or threonine

The substrate specificity of target enzymes, for example of MMP 2, MMP3 and MMP 9 and cathepsin B, H and L, is known (Netzel-Arnett et al. (1993), Biochemistry 32, 6427-6432, Shuja S., Sheahan, K., Murname, M. J. (1991), *Int. J. Cancer* 49, 341-346, Lah, T. T., Kos, J. (1998), *Biol. Chem.* 379, 125-130).

For example, in the case of MMP 2 and MMP 9, octapeptides (P4-P'4) have been identified, which octapeptides simulate the cleavage sequence of the collagen chain and are cleaved particularly efficiently by MMP 2 and 9:

Peptide
$P_4P_3P_2P_1P'_1P'_2P'_3P'_4$
Gly-Pro-Leu-Gly-Ile-Ala-Gly-Gln (SEQ ID NO:1)
Gly-Pro-Gln-Gly-Ile-Trp-Gly-Gln (SEQ ID NO:2)
(Netzel-Arnett et al., *Biochemistry* 32, 1993, 6427-764

The peptides are enzymatically cleaved exclusively at the $P_1$-$P'_1$ bond.

Furthermore, substrate-specific dipeptides having the sequence Arg-Arg- (SEQ ID NO:3), -Phe-Lys- (SEQ ID NO:4), Gly-Phe-Leu-Gly (SEQ ID NO: 5), Gly-Phe-Ala-Leu (SEQ ID NO: 6), and Ala-Leu-Ala-Leu (SEQ ID NO: 7) are known in the case of cathepsin B (Werle, B., Ebert, E., Klein, W., Spiess, E. (1995), *Biol. Chem. Hoppe-Seyler* 376, 157-164; Ulricht, B., Spiess, E., Schwartz-Albiez, R., Ebert, W. (1995), *Biol. Chem. Hoppe-Seyler* 376, 404-414.

The peptide sequence which contains the expected peptide cleavage site which is relevant for the target enzyme can also be constructed such that the expected peptide cleavage site is repeated several times, for example by means of:
-Gly-Pro-Leu-Gly-Ile-Ala-Gly-Gln-Gly-Pro-Leu-Gly-Ile-Ala-Gly-Gln (SEQ ID NO: 8) or
Phe-Lys-Phe-Lys-Phe-Lys-Phe-Lys-Phe-Lys (SEQ ID NO: 9)
or it is possible to integrate a repetitive peptide sequence which increases the distance between the protein-binding molecule and the relevant expected peptide cleavage site, as, for example, by means of:
-Gly-Gly-Gly-Gly-Gly-Gly-Gly-Gly-Gly-Gly-Gly-Gly-Phe-Lys-Phe-Lys- (SEQ ID NO: 10)

That which is crucial for the therapeutically and/or diagnostically effective substances which are to be used in the present invention is the fact that the expected peptide cleavage site which is relevant for the particular target enzyme occurs at least once in an oligopeptide. The oligopeptides which are listed above are representative examples for preparing therapeutically and/or diagnostically effective substances.

Therapeutically and/or diagnostically effective substances for the present invention which contain a cytokine can be prepared by reacting the cytokine with a protein-binding group-containing spacer molecule which possesses a carboxylic acid or an activated carboxylic acid:

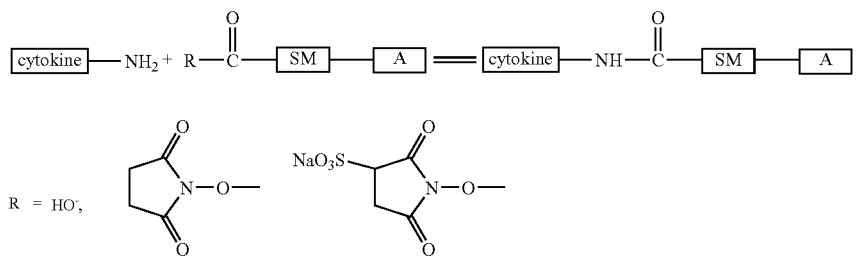

If the spacer molecule possesses a N-hydroxysuccinimide ester group (N-hydroxysuccinimide or N-hydroxysuccinimide-3-sulphonic acid sodium salt), it is reacted directly with the cytokine. The reaction of the cytokine with a protein-binding group-containing spacer molecule which possesses a carboxylic acid takes place in the presence of a condensing agent, such as N,N'-dicyclohexylcarbodiimide (DCC) or N-cyclohexyl-N'-(2-morpholinoethyl)carbodiimide metho-p-toluene-sulphonate (CMC), and, where appropriate, with addition of N-hydroxysuccinimide or N-hydroxysuccinimide-3-sulphonic acid sodium salt, to give the corresponding protein-binding cytokine derivatives. The cytokines which have been derivatized in this way are expediently purified by means of gel filtration chromatography. The skilled person is familiar with the above-described reactions (Bioconjugate Techniques, G. T. Hermanson, Academic Press, 1996).

Following the synthesis of the therapeutically and/or diagnostically effective substance, an injectable medicament preparation, which comprises the therapeutically and/or diagnostically effective substance, is produced in a suitable carrier liquid. The therapeutically and/or diagnostically effective substance is preferably present as a lyophilisate, with it being possible to add customary carriers and/or pharmaceutical auxiliary substances, such as polysorbates, glucose, lactose, mannose, citric acid, tromethamol, triethanolamine or aminoacetic acid, before or after the lyophilisation. The injectable medicament preparation must be produced in such a way that the protein-binding molecule is not deactivated, eliminated or hydrolysed by the process of dissolving in the injectable carrier liquid. Furthermore, care must be taken to ensure that the acid-labile bond in the therapeutically and/or diagnostically effective substance, which bond is an ester, acetal, ketal, imine, hydrazone, carboxylhydrazone or sulphonylhydrazone bond, is not hydrolysed. The protein-binding molecules which are used within the context of the present invention are base-sensitive, which means that the pH of the carrier liquid should not exceed a pH of 8.0. The pH is preferably in the range of pH 4.0-7.0, more preferably between pH 6.0 and pH 7.0. In addition, the carrier liquid must naturally be physiologically tolerated.

Carrier liquids which are preferred are virtually isotonic salt buffers, for example phosphate, acetate or citrate buffers, such as 0.004 M sodium phosphate, 0.15 M NaCl, pH 6.0-7.0, or 0.01 M sodium acetate, 0.14 M NaCl, pH 5.0-6.5. The carrier liquid used can also be an isotonic sodium chloride solution. The salt buffers may contain customary excipients and/or auxiliary substances, such as polysorbates, glucose, lactose, mannose, citric acid, tromethamol, triethanolamine or aminoacetic acid.

The solubility of the therapeutically and/or diagnostically effective substance in the injectable carrier liquid can be improved by means of pharmaceutical solvents, such as ethanol, isopropanol, 1,2-propylene glycol, glycerol, macrogols, polyethylene glycols and/or polyethylene oxides, or by means of solubility promoters, e.g. Tween, cremophore or polyvinylpyrrolidone. For this purpose, the therapeutically and/or diagnostically effective substance is either dissolved in the pharmaceutical solvent or solubility promoter and then diluted with a salt buffer, or else a carrier liquid, which contains the salt buffer and at least one pharmaceutical solvent or solubility promoter, is used directly for dissolving the therapeutically and/or diagnostically effective substance. In this connection, the concentration of the pharmaceutical solvents and/or solubility promoters do not exceed the quantities stipulated by the Arzheimittelgesetz (AMG) (Medicines Act).

The carrier liquid should preferably be selected such that the process of dissolving the therapeutically and/or diagnostically effective substance in the carrier liquid is concluded after a few minutes, such that an injectable medicament preparation is made available at the patient's bedside.

It is also possible, in addition, for a carrier molecule, such as one of those mentioned at the outset, to be brought into contact with the effective substance, with the effective substance being able to bind to this carrier molecule. According to another embodiment, the present invention consequently encompasses the step of bringing the carrier molecule and the protein-binding therapeutically and/or diagnostically effective substance into contact ex vivo and subsequently administering them parenterally. In this way, it is possible, if desired or if necessary, to improve the selectivity of the therapeutically and/or diagnostically effective substance for a carrier molecule, for example for albumin. The carrier molecules are preferably selected from the carrier molecules which have been mentioned, in particular serum proteins.

The therapeutically and/or diagnostically effective substance which has been prepared in accordance with the process according to the invention is consequently suitable for treating cancer diseases, virus diseases, autoimmune diseases, acute or chronic inflammatory diseases and/or diseases which are caused by bacteria, fungi or other microorganisms.

Another part of the subject-matter of the present invention is a therapeutically and/or diagnostically effective substance containing at least one active compound, which substance is characterized in that it possesses at least one protein-binding molecular residue which is linked to the active compound by means of a spacer, with the spacer, or the bond between the spacer and the active compound, being hydrolytically or enzymically cleavable in the body in a pH-dependent manner, resulting in the release of the active compound, with the active compound not being a cytostatic agent.

Yet another part of the subject-matter of the present invention is a diagnostically effective substance containing at least one diagnostic agent, which substance is characterized in that it [lacuna] at least one protein-binding molecular residue which is linked to the diagnostic agent by means of a spacer, with the spacer, or the bond between the spacer and the diagnostic agent, being hydrolytically or enzymically cleavable in the body in a pH-dependent manner, resulting in the release of the diagnostic agent. As mentioned above, the diagnostic agent preferably comprises one or more radionuclides, one or more ligands comprising radionuclides, one or more positron emitters, one or more NMR contrast agents, one or more fluorescent compound(s) and/or one or more contrast agents in the near IR range.

Another embodiment of the present invention relates to a diagnostic kit which comprises a protein-binding, diagnostically effective substance according to the invention, where appropriate together with the carrier molecule and pharmaceutically acceptable auxiliary substances, carrier substances and/or diluents, which are selected, in particular, from those mentioned above. The diagnostic kit according to the invention can preferably be used for detecting the diseases as defined above or for detecting carrier molecules and/or their distribution in the body.

Yet another part of the subject-matter of the present invention is a process for producing an injectable medicament preparation, comprising a diagnostically effective substance which is dissolved in an injectable carrier liquid, which process is characterized in that a compound comprising a diagnostic agent and at least one protein-binding molecular residue is used as the diagnostically effective substance. A diagnostic agent can be one of the abovementioned compounds, for example one or more radionuclides, one or more ligands comprising radionuclides, one or more positron emitters, one or more NMR contrast agents, one or more fluorescent compound(s) and/or one or more contrast agents in the near IR range. The diagnostic agent and the at least one protein-binding molecular residue can also be linked by means of a spacer. In this case, preference is given to the spacer, or the bond which links the two components, not being cleavable. Examples of bonds which are not cleavable in the body, and which can be present in the case of the bond to the diagnostically effective substance, are amide bonds, saturated and unsaturated carbon-carbon bonds or bonds between carbon and a heteroatom, i.e. —C—X—, where X is preferably O, N, S or P. An amide bond is a preferred bond. Preference is given to the therapeutically effective substance being released since, as a rule, the low molecular weight active compound must interact with its molecular target in order to express its pharmacological activity. In the case of diagnostically effective substances, on the other hand, it is not absolutely necessary for the protein-bound diagnostic agent to be released; however, this may occur. According to the invention, therefore, the diagnostically effective substance can be additionally bound to the spacer molecule by way of a bond which is not cleavable in the body or be bound directly to the protein-binding group without any spacer molecule SM being present.

The following examples explain the invention in more detail.

EXAMPLE 1

Preparation of DOXO-HYD

The pharmacologically active substance depicted below (abbreviated to DOXO-HYD) consists of the cytostatic agent doxorubicin, a maleimide group as the protein-binding molecule PM, and a phenylacetylhydrazone spacer as the spacer molecule SM. The bond between doxorubicin and the spacer molecule SM is an acid-labile carboxyl-hydrazone bond:

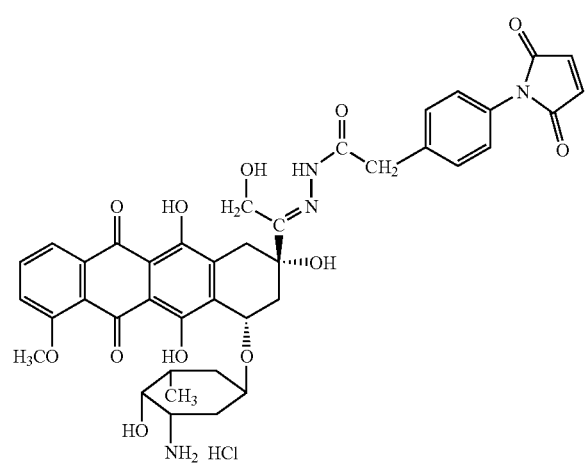

10.51 mg of DOXO-HYD are dissolved, by shaking, in 2.0 ml of 1,2-propylene glycol and this solution is subsequently diluted with 8.0 ml of phosphate buffer (0.004 M sodium phosphate, 0.15 M NaCl—pH 6.5) and homogenized (concentration of DOXO-HYD in the carrier liquid≈1300 μM). The injectable medicament preparation of DOXO-HYD which had been produced in this way was immediately administered intravenously to experimental animals (see below).

EXAMPLE 2

Binding of DOXO-HYD to Human Plasma

After DOXO-HYD arrives in the blood stream, it binds to serum proteins, preferentially to serumalbumin, such that DOXO-HYD is present, inter alia, as an acid-labile albumin-doxorubicin conjugate.

Figure 1A:
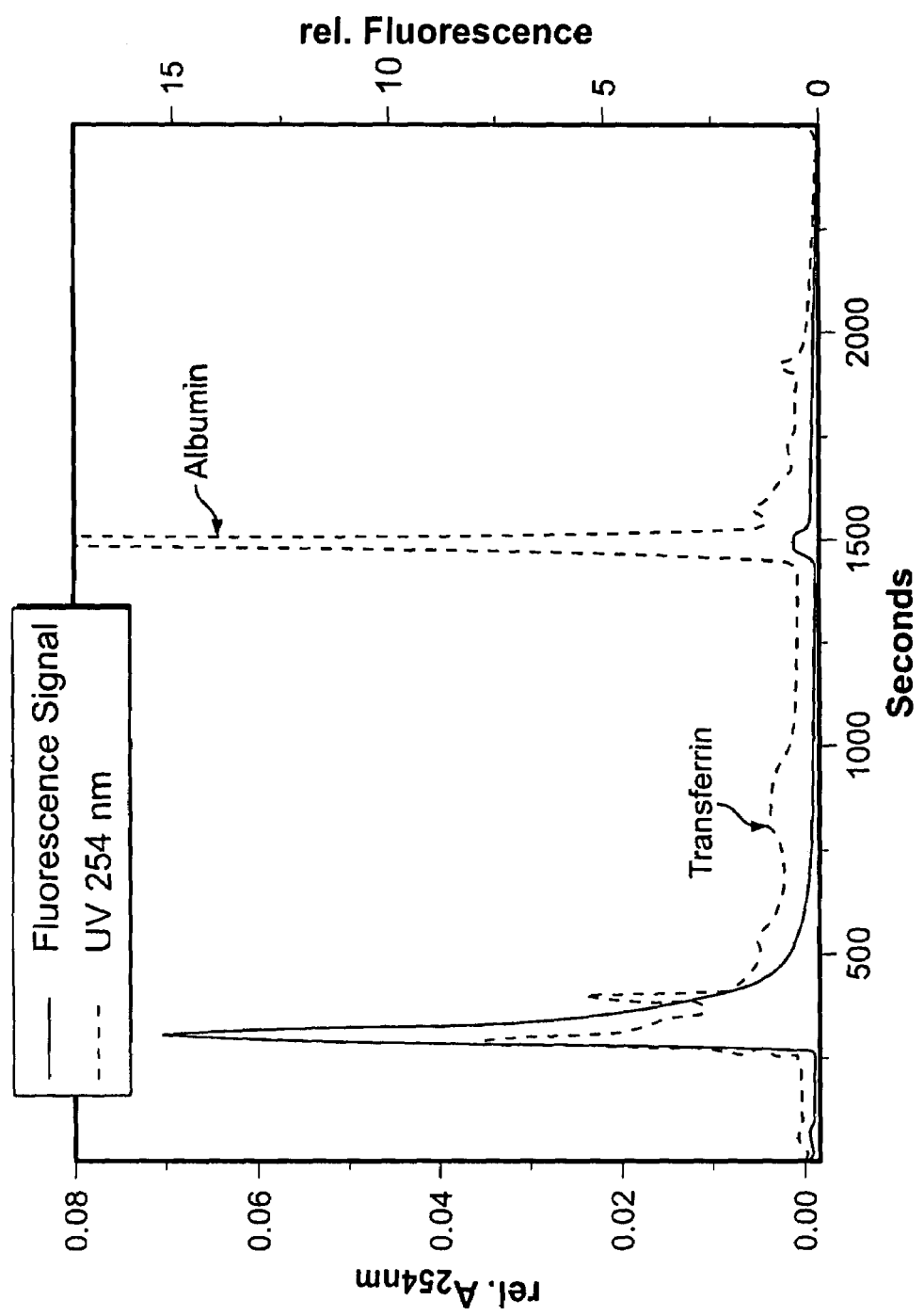

Studies of the incubation of human blood plasma with DOXO-HYD at 37° C. show that most of the DOXO-HYD is covalently bonded to the albumin after 5 minutes of incubation (FIG. 1A).—in contrast to free doxorubicin (FIG. 1B). This situation is depicted in the chromatograms of FIGS. 1A and 1B.

In this experiment, the plasma sample was separated, after the incubation had taken place, on a POROS®-20 anion exchange column (the proteins were detected at 254 nm while the anthracycline was detected by fluorescence).

EXAMPLE 3

The Activity of DOXO-HYD In vivo

The biological data listed below clarify the in vivo activity of DOXO-HYD as compared with that of free doxorubicin: in what is termed the RENCA (renal cell carcinoma) model, doxorubicin and DOXO-HYD were compared with each other, at approximately equitoxic doses, as regards their antitumour activity (intravenous therapy 10 days after injecting about 1 million kidney carcinoma cells into the left kidney).

Animals: Balc/c mice, female; Tumour: RENCA, renal cell carcinoma

Therapy: Intravenous (i.v.) on day (d) 10, 13, 17 and 20, end of experiment on d24

| Number of Mice | Substance | Dose | Average decrease in body weight (%) d 1-24 |
|---|---|---|---|
| 10 | Control | | |
| 10 | Doxorubicin | 4 × 10 mmol/kg | −15 |
| 10 | DOXO-HYD | 4 × 20 mmol/kg | −15 |

The results of this experiment are depicted below. DOXO-HYD exhibits very good antitumour activity and achieves a marked reduction in kidney tumour volume and in the number of lung metastases as compared with the control group and the doxorubicin-treated group.

Figure 2:
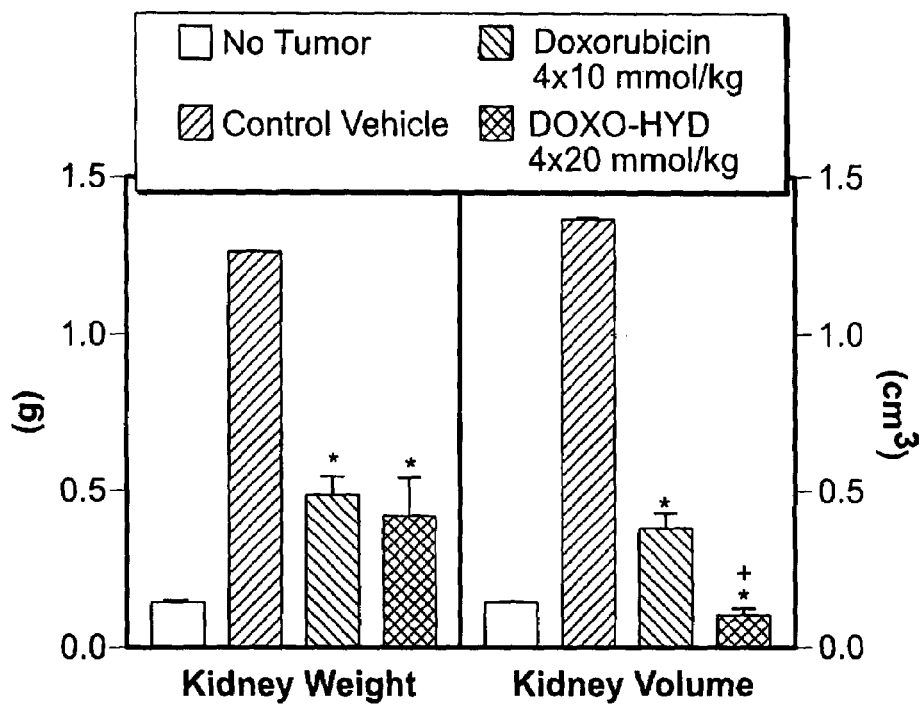
FIG. 2A shows the weight and volume of the kidneys and kidney tumors of Example 4.
FIG. 2B shows the lung weight and number of lung metastases according to Example 4.
Figure 2A:
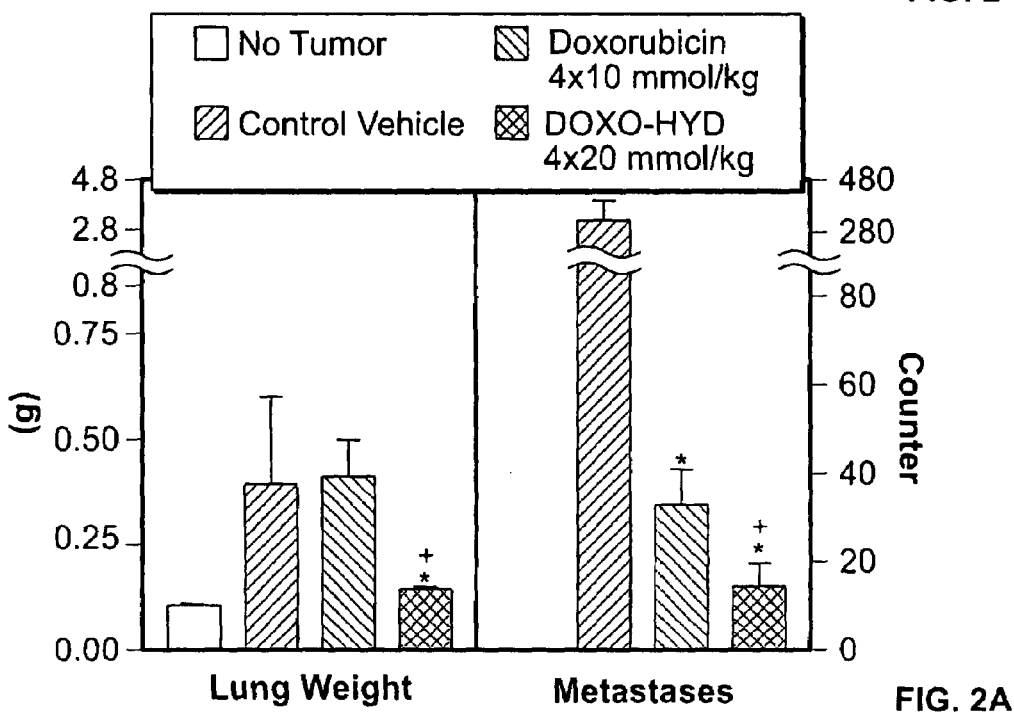

The weight and volume of the kidneys and kidney tumours and the number of lung metastases as shown in FIGS. 2A and 2B.

The symbol * in FIGS. 2A and 2B refers to a significant in relation to the control group (control).

The symbol + in FIGS. 2A and 2B refers to significant in relation to the group which received doxorubicin.

EXAMPLE 4

Binding of DOXO-EMHC to Albumin in Human Plasma 1.6 mg of the 6-maleimidocaproic acid hydrazone derivative of doxorubicin (abbreviated to DOXO-EMHC) having the following structural formula

Figure 3:
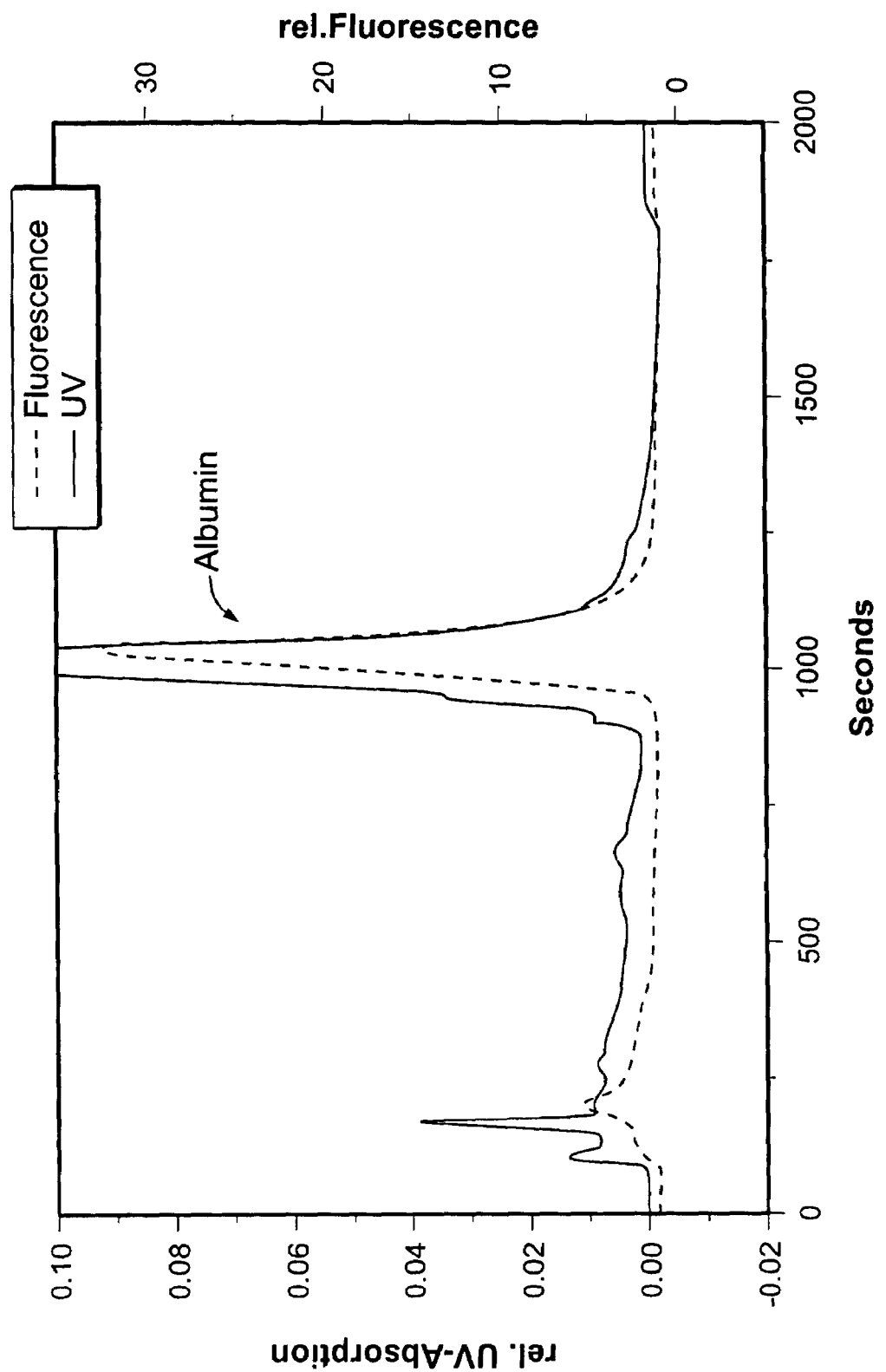
FIG. 3 is a chromatogram showing binding of DOXO-EMHC according to Example 4.

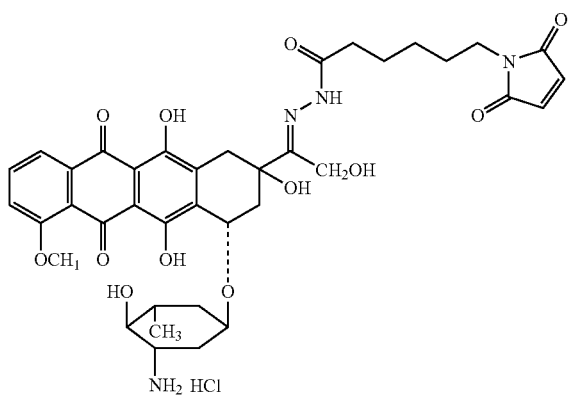

are dissolved, at room temperature, in 1.0 ml of phosphate buffer (0.15 M NaCl, 0.004 M sodium phosphate, pH 6.5) (2000 μM solution). When 250μ of this solution are incubated for 30 seconds, at 37° C., with 1.0 ml of human plasma and the sample is subsequently separated on a weak anion exchanger (from POROS®), it is found that the majority of the DOXO-EMHC is bound to albumin (see FIG. 3).

EXAMPLE 5

Binding of an MMP9-Cleavable Doxorubicin-Maleimide-Peptide Derivative (2) to Albumin Following a One-Minute Incubation with Human Plasma The doxorubicin-maleimide-peptide derivative (2) was prepared in accordance with the following reaction equation:

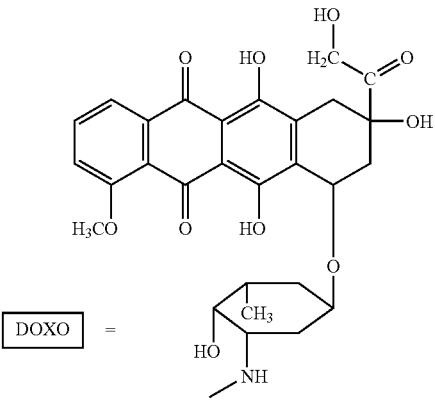

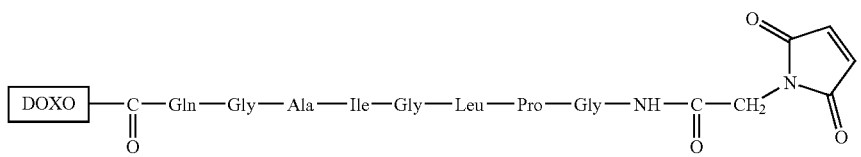

2

DMF, HPTU
N-methylmorpholine
hydroxybenzotriazole

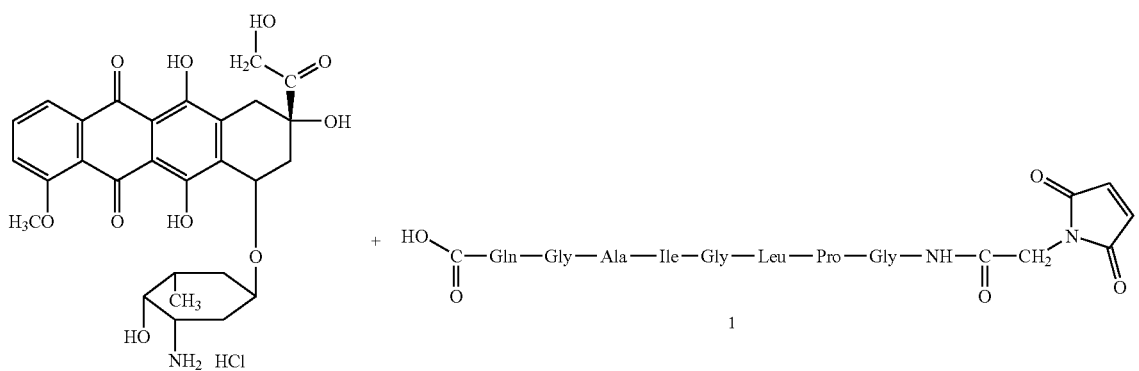

1

In this preparation, the maleimidoglycine-derivatized octapeptide Gln-Gly-Ala-Ile-Gly-Leu-Pro-Gly (SEQ ID NO: 11) 1 (Mr 848, prepared by Bachem AG, Switzerland using solid-phase synthesis) is reacted with doxorubicin in accordance with the following protocol:

25 mg of 1 (as the trifluoroacetate salt), dissolved in 500 μl of DMF, 33.5 mg of O-benzotriazole-N,N,N',N'-tetramethyluronium hexafluorophosphate (HPTU), dissolved in 200 μl of DMF, 11.9 mg of hydroxybenzotriazole hydrate, dissolved in 100 μl of DMF, and 16.2 μl of N-methylmorpholine are added to a slightly turbid solution of 17.1 mg of doxorubicin in 3 ml of DMF and the mixture is subsequently stirred in the dark at RT for 18 h. DMF was removed under high vacuum and the solid taken up in 20 ml of methanol; this solution was then filtered and concentrated down to 1 ml in vacuo. After purifying on silica gel (ethyl acetate/methanol 2/1), 5 mg of 2 were obtained.

Figure 4:
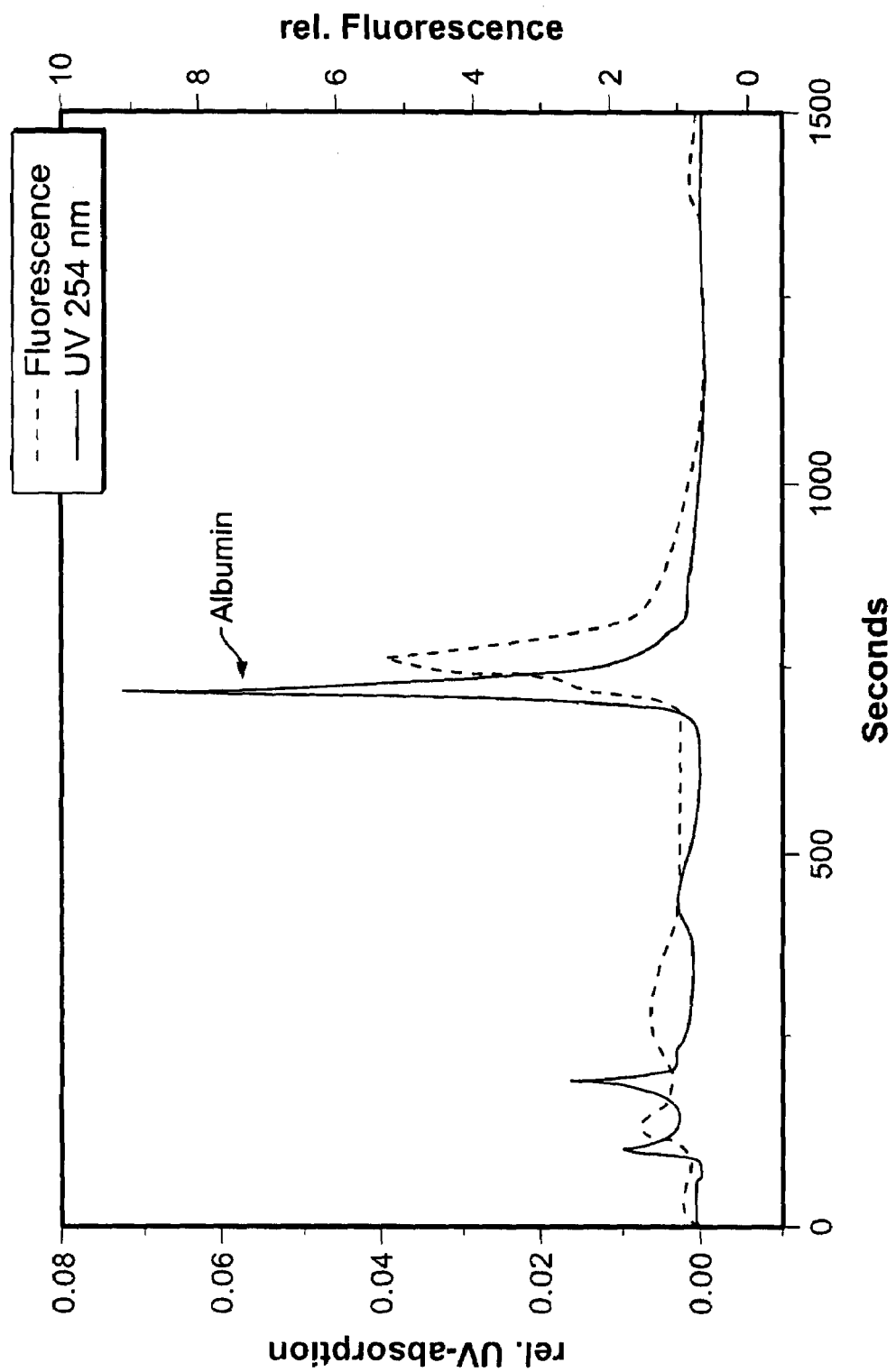
FIG. 4 is a chromatogram showing albumin binding of (Mr1374) according to Example 5.

Incubation Study Using Human Plasma 1.4 mg of 2 (Mr 1374) are dissolved, at room temperature, in 1.0 ml of phosphate buffer (0.15 M NaCl, 0.004 M sodium phosphate, pH 6.5) (1000 μm solution). When 300 μl of this solution is incubated for 60 seconds, at 37° C., with 1.0 ml of human plasma and the sample is subsequently separated on a weak anion exchanger (from POROS®), it is found that the majority of 2 is bound to albumin (see FIG. 4).

The peptide sequence Gln-Gly-Ala-Ile-Gly-Leu-Pro-Gly (SEQ ID NO: 11) is recognized by the matrix metalloprotease MMP9 and cleaved between isoleucine and glycine. This was demonstrated by the following experiment: 200 μl of a 100 μM solution of the albumin conjugate of 2 having the following structure (abbreviated to HSA-2):

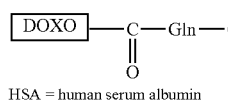
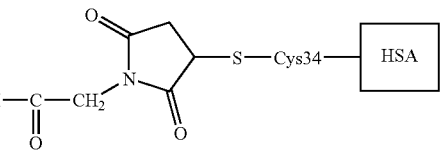

Figure 5B:
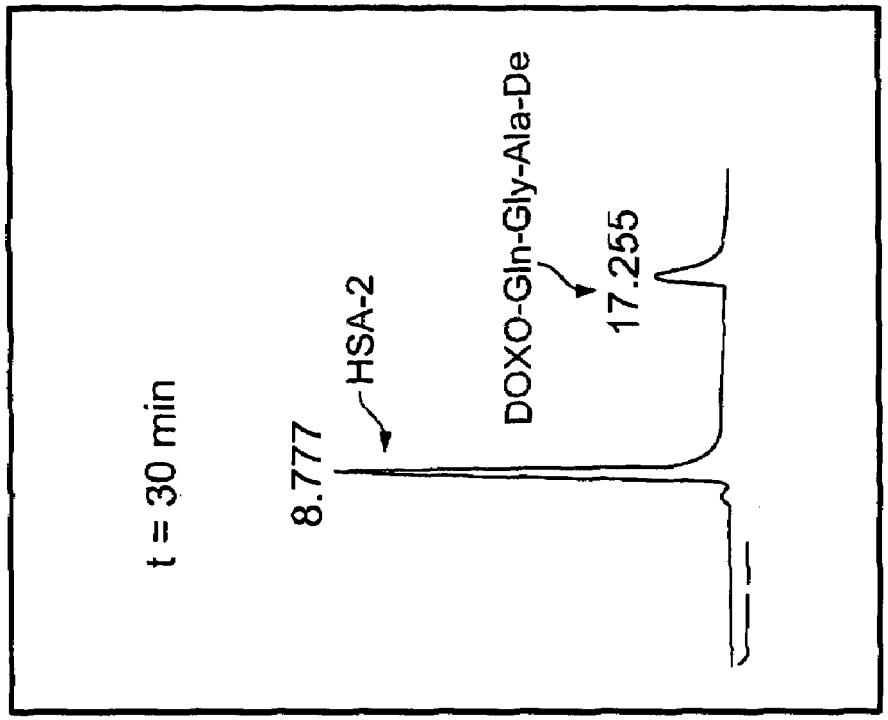
FIGS. 5A and 5B are chromatograms of HSA-2 at t=0 (FIG. 5B) and after having been incubated with activated mmp9 for 30 minutes (FIG. 5B) according to Example 5.
Figure 5A:
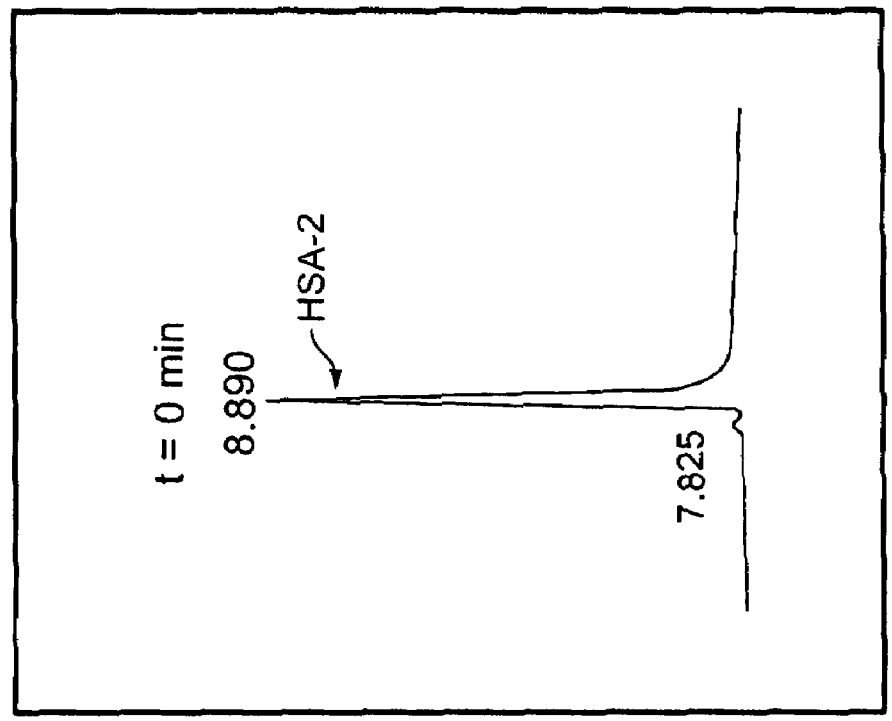

HSA = human serum albumin which was prepared by the method described in German Patent Application A19926475.9, dated 10 Jun. 1999, was incubated, at 37° for 30 minutes, with trypsin/aprotinin-activated MMP9 (2 mU, from Calbiochem, Germany). The release of DOXO-Gln-Gly-Ala-Ile after this time is depicted in the following chromatograms. The figure shows the chromatogram of HSA-2 at t=0 (separation by means of HPLC exclusion chromatography using a Biosil 250 SEC column supplied by Biorad, detection at λ=495 nm) and after having been incubated with activated MMP9 for 30 minutes (see FIGS. 5A and 5B).

EXAMPLE 6

Binding of Fluoresceinmaleimide to Albumin in Human Plasma

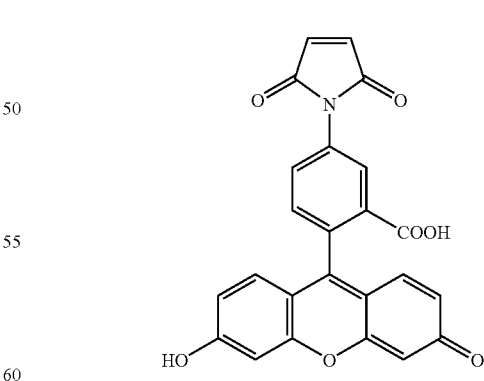

Figure 6:
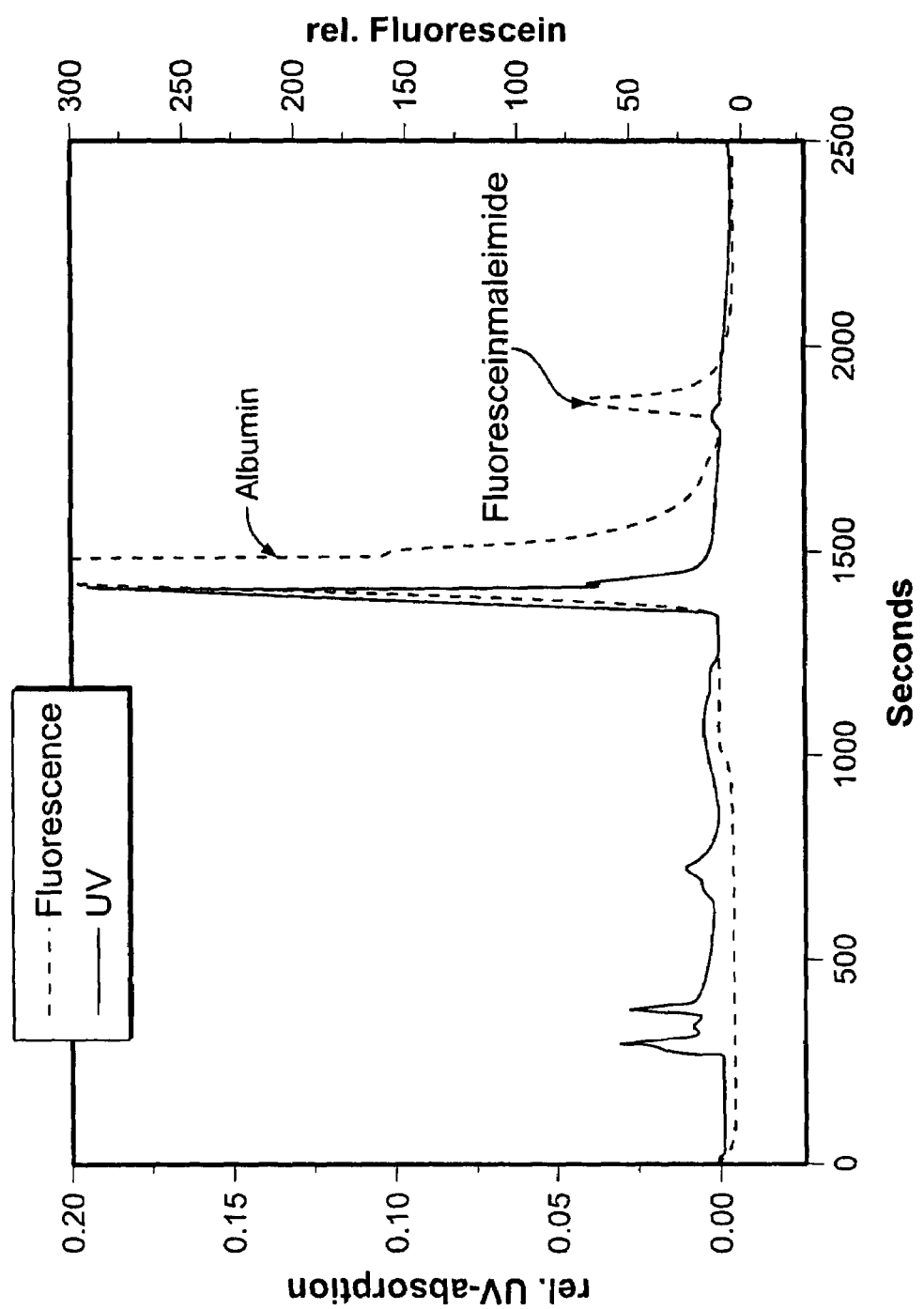
FIG. 6 is a chromatogram showing albumin binding of fluoresceinmaleimide according to Example 6.

After incubating 250 μl of a 100 μM solution of fluoresceinmaleimide solution (phosphate buffer=0.15 M NaCl, 0.004 M sodium phosphate, pH 5.0) with 1.0 ml of human plasma for 5 minutes and subsequently separating the sample by means of gel filtration chromatography (Superdex® 200, Pharmacia), it is found that the majority of the fluoresceinmaleimide is bound to albumin (see FIG. 6).

The invention claimed is:

1. A process for producing an injectable medicament preparation comprising: dissolving at least one therapeutically effective substance in an injectable carrier liquid, wherein the therapeutically effective substance comprises an active compound selected from the group consisting of cytostatic agent, a cytokine, an immunosuppressive agent, a virostatic agent, an antirheumatic agent, an analgesic, an antiinflammatory agent, an antibiotic, an antimycotic agent, a signal transduction inhibitor, an angiogenesis inhibitor or a protease inhibitor and at least one covalently protein-binding molecular residue selected from the group consisting of maleimide, haloacetamide, haloacetate, pyridylthio, N-hydroxysuccinimide ester, isothiocyanate, disulphide, vinylcarbonyl, aziridine and acetylene, which are linked by a spacer comprising an organic molecular residue, which contains at least one aliphatic carbon chain, or an aliphatic carbon ring having 1-12 carbon atoms, some of which can be replaced with oxygen, or at least one aromatic moiety, in which the spacer, or the bond between the active compound and the spacer, can be cleaved hydrolytically or enzymatically in the body of a subject in a pH-dependent manner.

2. The process according to claim 1, wherein the spacer, or the bond between the active compound and the spacer, can be cleaved in the body of the subject, with the release of the active compound or of a derivative of the active compound.

3. The process according to claim 1, wherein the active compound is doxorubicin.

4. The process according to claim 1, wherein the active compound is selected from the group consisting of anthracyclines, nitrogen mustard derivatives, alkylating agents, purine or pyrimidine antagonists, folic acid antagonists, taxanes, camptothecins, podophyllotoxin derivatives, vinca alkaloids, calicheamicins, maytansinoids or cis-configured platinum (II) complexes.

5. The process according to claim 1, wherein said covalently protein-binding molecular residue is phenylacetylhydrazone.

6. The process according to claim 1, wherein said covalently protein-binding molecular residue is a maleimide.

7. The process according to claim 3, wherein the spacer is phenylacetylhydrazone.

8. The process according to claim 7, wherein said protein-binding molecular residue is maleimide.

9. The process according to claim 1, further comprising a carrier molecule.

10. The process according to claim 9, wherein the carrier molecule and the therapeutically or diagnostically effective substance are brought into contact ex vivo.

* * * * *

SEQUENCE LISTING

<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: example peptide

<400> SEQUENCE: 1

Gly Pro Leu Gly Ile Ala Gly Gln
1               5

<210> SEQ ID NO 2
<211> LENGTH: 8
<212> TYPE: PRT
<213> ORGANISM: Artificial Sequence
<220> FEATURE:
<223> OTHER INFORMATION: example peptide

<400> SEQUENCE: 2

Gly Pro Gln Gly Ile Trp Gly Gln
1               5

<210> SEQ ID NO 3
<211> LENGTH: 2
<212> TYPE: PRT
<213> ORGANISM: Artificial Sequence
<220> FEATURE:
<223> OTHER INFORMATION: substrate-specific peptide

<400> SEQUENCE: 3

Arg Arg
1

<210> SEQ ID NO 4
<211> LENGTH: 2
<212> TYPE: PRT
<213> ORGANISM: Artificial Sequence
<220> FEATURE:
<223> OTHER INFORMATION: substrate-specific peptide

<400> SEQUENCE: 4

Phe Lys
1

<210> SEQ ID NO 5
<211> LENGTH: 4
<212> TYPE: PRT
<213> ORGANISM: Artificial Sequence
<220> FEATURE:
<223> OTHER INFORMATION: substrate-specific peptide

<400> SEQUENCE: 5

Gly Phe Leu Gly
1

<210> SEQ ID NO 6
<211> LENGTH: 4
<212> TYPE: PRT
<213> ORGANISM: Artificial Sequence
<220> FEATURE:
<223> OTHER INFORMATION: substrate-specific peptide -continued

```
<400> SEQUENCE: 6

Gly Phe Ala Leu
1

<210> SEQ ID NO 7
<211> LENGTH: 4
<212> TYPE: PRT
<213> ORGANISM: Artificial Sequence
<220> FEATURE:
<223> OTHER INFORMATION: substrate-specific peptide

<400> SEQUENCE: 7

Ala Leu Ala Leu
1

<210> SEQ ID NO 8
<211> LENGTH: 16
<212> TYPE: PRT
<213> ORGANISM: Artificial Sequence
<220> FEATURE:
<223> OTHER INFORMATION: example peptide

<400> SEQUENCE: 8

Gly Pro Leu Gly Ile Ala Gly Gln Gly Pro Leu Gly Ile Ala Gly Gln
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: example peptide

<400> SEQUENCE: 9

Phe Lys Phe Lys Phe Lys Phe Lys Phe Lys Phe Lys
1               5                   10

<210> SEQ ID NO 10
<211> LENGTH: 16
<212> TYPE: PRT
<213> ORGANISM: Artificial Sequence
<220> FEATURE:
<223> OTHER INFORMATION: example peptide

<400> SEQUENCE: 10

Gly Gly Gly Gly Gly Gly Gly Gly Gly Gly Gly Gly Phe Lys Phe Lys
1               5                   10                  15

<210> SEQ ID NO 11
<211> LENGTH: 8
<212> TYPE: PRT
<213> ORGANISM: Artificial sequence
<220> FEATURE:
<223> OTHER INFORMATION: maleimidoglycine-derivatized octapeptide

<400> SEQUENCE: 11

Gln Gly Ala Ile Gly Leu Pro Gly
1               5
```